United States Patent [19]

Hanzawa

[11] Patent Number: 4,509,943
[45] Date of Patent: Apr. 9, 1985

[54] INFUSION CONTROL APPARATUS

[75] Inventor: Yoshiki Hanzawa, Fujinomiya, Japan

[73] Assignee: Terumo Kabushiki Kaisha, Tokyo, Japan

[21] Appl. No.: 404,860

[22] Filed: Aug. 3, 1982

[30] Foreign Application Priority Data

Aug. 10, 1981 [JP] Japan .................................. 56-125045

[51] Int. Cl.³ .................................................. A61M 5/16
[52] U.S. Cl. ............................. 604/31; 128/DIG. 13;
604/67; 73/861.41
[58] Field of Search ............... 128/DIG. 13; 604/151,
604/156, 149, 67, 31; 73/861.41

[56] References Cited

U.S. PATENT DOCUMENTS

| | | | |
|---|---|---|---|
| 3,890,968 | 6/1975 | Pierce et al. | 128/DIG. 13 |
| 3,990,443 | 11/1976 | Fletcher | 128/DIG. 13 |
| 4,018,362 | 4/1977 | Ubaud | 128/DIG. 13 |
| 4,037,598 | 7/1977 | Georgi | 128/DIG. 13 |
| 4,094,318 | 6/1978 | Burke et al. | 128/DIG. 13 |

Primary Examiner—Lee S. Cohen
Assistant Examiner—Steven Falk
Attorney, Agent, or Firm—Frishauf, Holtz, Goodman & Woodward

[57] ABSTRACT

An infusion control apparatus senses drops of an infusion liquid by way of a variation in the quantity of light received from a light source after the light passes through a drop chamber. When drops of the liquid are not sensed over a predetermined period of time, a cut-off operation for closing off an infusion liquid flow passage starts and takes priority over other forms of control. When a drop-wise flow of the liquid is sensed during the cut-off operation, the flow passage closing action is interrupted and a transition is made to resume control wherein the liquid drop interval is computed from an input signal based on the variation in received light, and the liquid flow passage is adjusted so that the drop interval is made to approach a set value.

7 Claims, 5 Drawing Figures

INFUSION CONTROL APPARATUS

BACKGROUND OF THE INVENTION

1. Field of the Invention

This invention relates to an infusion control apparatus and, more particularly, to an apparatus for controlling the administration of an infusion liquid to a living body in a drop-wise manner based upon gravity feed.

2. Description of the Prior Art

Conventionally, an infusion control apparatus of the above type includes means for generating a succession of drop signal pulses in response to the drop-wise flow of the infusion liquid, means for setting a desired liquid drop rate and for generating a reference clock which corresponds to the set drop rate, and means for comparing the actually measured drop interval, found by counting the reference clock pulses between generated drop signal pulses, against a reference value, and for adjusting the liquid flow passage in accordance with any disparity detected by the comparison operation.

When a liquid is infused into a vein located in the patient's arm, by way of example, there are situations where the liquid flow passage is released from a closed or nearly closed state, converting the drop-wise flow of liquid into a continuous flow. This can be caused by the patient bending and then straightening his arm, by accidental twisting of the flexible tubing carrying the liquid, or for some other reason. When such a situation arises, it is essential for the safety of the patient that the abnormal condition be detected rapidly and that the flow rate be restored to the set drop rate. Heretofore, it has been general practice to achieve this by detecting the absence of the drop signal pulses, namely the absence of discrete liquid drops, as will be the case when the liquid is flowing continuously. Upon such detection, the flow passage is immediately closed and an audible alarm issued to attract the attention of a nurse or other attendant, who then remedies the problem, resets the alarm and restores the apparatus to the proper condition to provide the correct drop-wise flow, namely the set drop rate. Such an arrangement is beset by a number of difficulties, namely the need for human intervention, the frequent alarm which may upset the patient, and the time required to restore the proper conditions. Although a system is available for detecting continuous flow based on the drop signal pulses by utilizing a change in electrical capacitance which occurs when the continuous flow is detected by means of an electrode provided on the drop chamber, the application of this system is limited owing to differences in the size and shape of the drop chamber. Another contemplated method of detecting continous flow based on the drop signal pulses is to intercept, by means of a photoelectric converting element, a beam of light from a light source after passage through the drop chamber, and then utilize the disparity in light transmission that would develop between the nearly spherical droplets which prevail in drop-wise flow, and the substantially columnar liquid stream that is produced by continuous flow. A problem encountered with this method, however, is the difficulty in discriminating between the complete absence of flow on one hand, and continuous flow on the other, since there is so little difference in the light transmission characteristics between them. Accordingly, the present state of the art is such that the photoelectric converting element is in general use for detecting discrete drops, but is not successful in detecting continuous flow.

SUMMARY OF THE INVENTION

Accordingly, an object of the present invention is to provide an infusion control apparatus devoid of the problems encountered in the prior art.

Another object of the present invention is to provide an infusion control apparatus which is extremely safe and easy to operate, and capable of detecting continuous flow and of restoring the normal drop-wise flow conditions immediately.

Another object of the present invention is to provide an infusion control apparatus wherein contionus flow of the infusion liquid and the depletion of the infusion liquid in a liquid reservoir are clearly discriminated by logic means, whereby the apparatus is held in an inoperative state when the latter condition is detected.

A further object of the present invention is to provide an infusion control apparatus wherein, by adopting a photoelectric converting system for detecting drop-wise feed of the infusion liquid, no limitations are imposed by the shape of the drop chamber or any other member serving as the base for attaching the converting element.

In accordance with the present invention, these and other objects are attained by providing an infusion control apparatus which comprises input means for forming an input signal on the basis of a change in a quantity of received light caused by falling drops of an infusion liquid, means responsive to a control signal for adjusting the infusion liquid flow passage, drop interval control means adapted to evaluate the interval between the falling drops of infusion liquid for producing a control signal operative to establish a drop interval adjustment mode for bringing the interval into agreement with a set value, means for establishing a liquid cut-off mode to close off the flow of infusion liquid through the flow passage upon detecting absence of the input signal over a predetermined period of time, and means for effecting a changeover from the liquid cut-off mode to the drop interval adjustment mode upon detecting the input signal after initiation of the cut-off mode.

The infusion control apparatus further includes priority deciding means for giving the output from the means for establishing a liquid cut-off mode, a higher order of priority than the output from the drop interval control means. The input means comprises a light source and a light-receiving element disposed to confront each other across a transparent drop chamber in which the infusion liquid drops, the light-receiving element receiving light from the light source. More specifically, the means for establishing a liquid-cut off mode includes alarm means actuated upon detecting an absence of the input signal over a predetermined period of time, and the means for adjusting the flow passage comprises sensing means for sensing full closure of the flow passage, and inhibit means for inhibiting an output from the drop interval control means and from the means for establishing a liquid cut-off mode, in response to detection of full closure by the sensing means.

Other features and advantages of the invention will be apparent from the following description taken in conjunction with the accompanying drawings in which like reference characters designate the same or similar parts throughout the figures thereof.

DESCRIPTION OF THE PREFERRED EMBODIMENT

Figure 1:
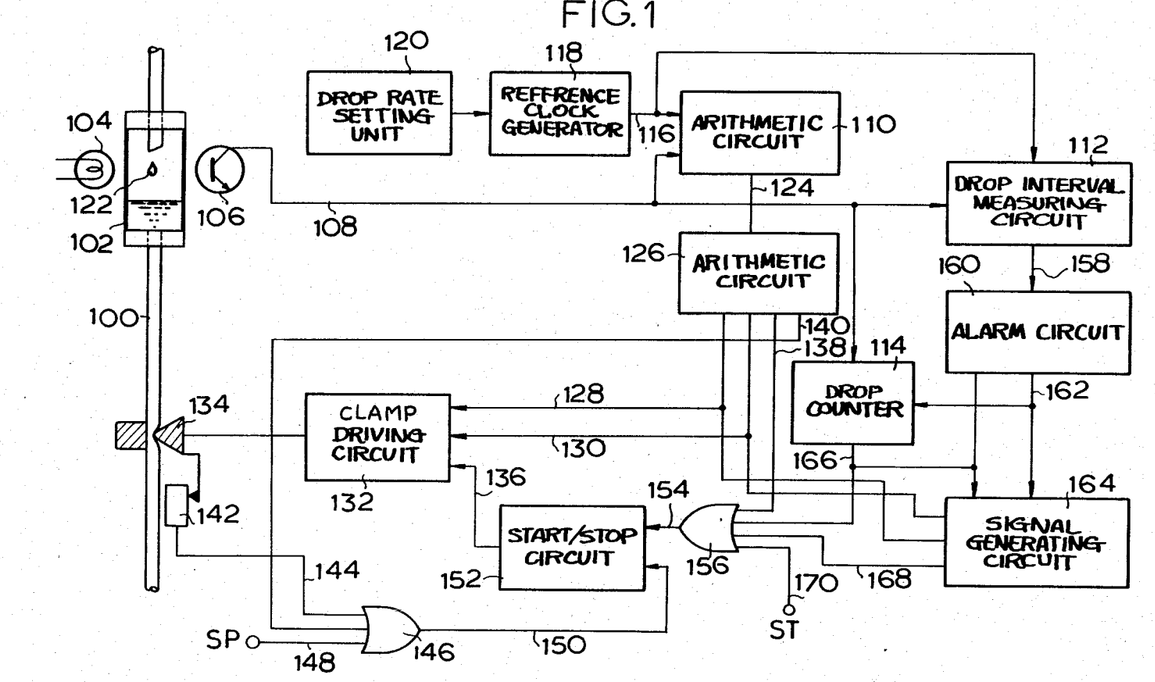
FIG. 1 is a block diagram illustrating an embodiment of an infusion control apparatus according to the present invention.

Referring to FIG. 1, an apparatus of the type to which the present invention appertains typically is adapted to infuse a fluid such as liquid medication into the vein of a living body in a drop-wise manner. To this end, the apparatus includes a flexible tube 100 for feeding the liquid to, e.g., a hypodermic needle, a transparent drop chamber 102 to which the tube 100 is connected, a light source 104 such as a light-emitting diode, and a photoelectric converting element 106, such as a phototransistor, so disposed as to receive the light beam from the light source after passage through the drop chamber 102. The output lead of the element 106 is connected to an arithmetic circuit 110 for evaluating an error, as will be described below, a circuit 112 for measuring the drop interval, and a drop counter 114. The other input to the arithmetic circuit 110, arriving on lead 116, is the output of a reference clock signal generating circuit 118 the input of which is connected to the output of a drop rate setting unit 120. The drop rate setting unit 120 includes a switch operated by an attendant for manually setting the desired drop rate. The drop rate represents the rate at which drops of the infusion liquid, one of which is indicated at numeral 122, fall within the drop chamber 102, namely the number of drops that fall per unit of time.

The reference clock generating circuit 118 produces, on lead 116, a reference clock 200 having a repetition frequency proportional to the set drop rate. The reference clock is shown in (A) of FIG. 2. The reference clock frequency is set to a value which is, by way of example, 30 times the frequency obtained by converting the drop rate, set in the manner described above, into a figure expressed in seconds.

Figure 2:
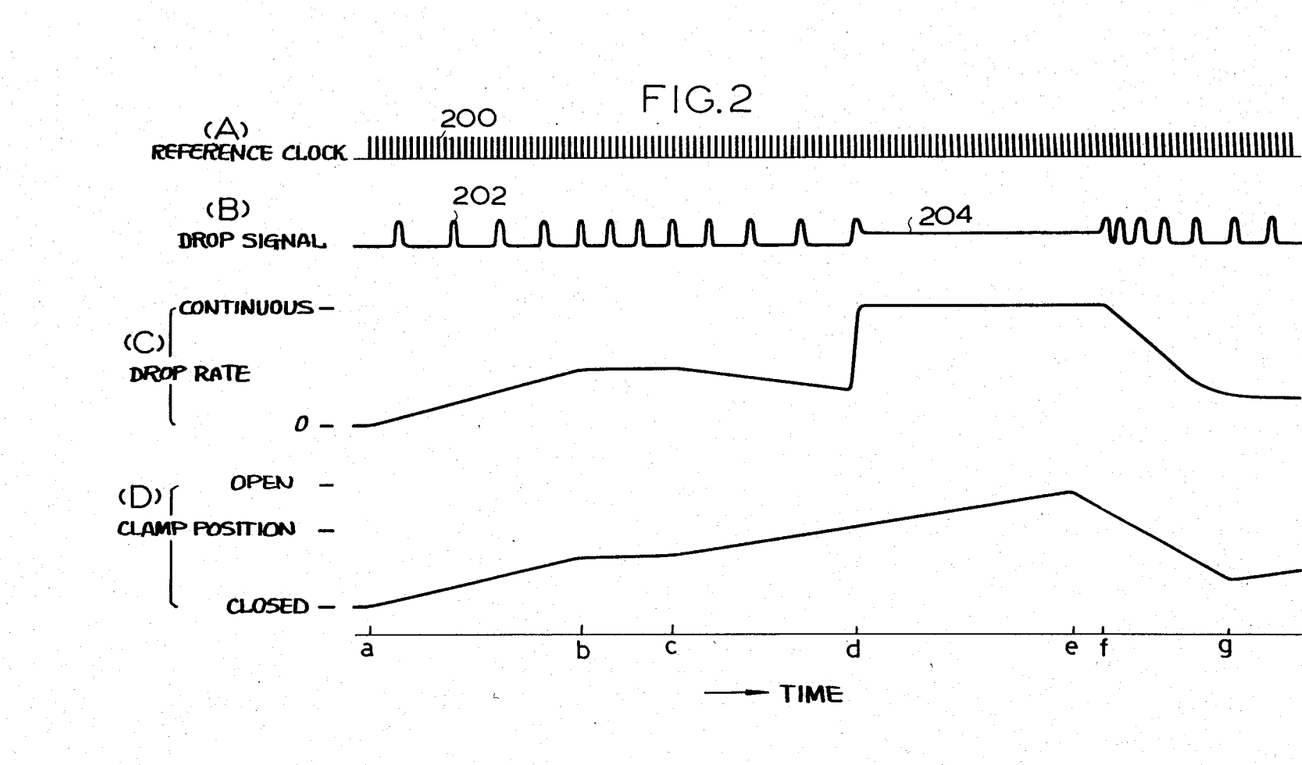
FIG. 2 is a waveform diagram useful in describing the operation of the apparatus shown in FIG. 1.

The photoelectric converting element 106 receives the light beam from the light-emitting element 104 following passage through the drop chamber 102. When a drop of liquid 122 falls within the drop chamber, the light from the element 104 is totally reflected by the nearly spherical liquid drop so that there is a change in the amount of light received by the element 106. The element 106 converts the behavior of the received light into an electrical signal 202 which appears on lead 108. The signal, which typically has the waveform shown at (B) in FIG. 2, is referred to as a drop signal and is composed of pulses produced each time a drop is detected in the drop chamber. When the drop rate increases to reduce the time interval between drops, the period of the drop signal pulses 202 shortens accordingly. Steadily increasing the drop rate will eventually cause the liquid falling within the drop chamber to form a continuous, columnar-like flow rather than a drop-wise flow.

Since the liquid having the columnar shape will exhibit a full reflection characteristic different from that of a spherical droplet 122, there will be a change in the quantity of light received by the photoelectric converting element 106. The drop signal produced by the element 106 on lead 108 will therefore have the appearance shown, by way of example, at numeral 204 in (B) of FIG. 2. In short, the pulsed waveform indicated at 202 in FIG. 2 is replaced in this case by a flattened or level continuous waveform 204.

The arithmetic circuit 110 is designed to evaluate any difference or error that may develop between the set drop rate and the actual detected drop rate. To this end, the arithmetic circuit 110 is adapted to measure the time interval of the drop signal pulses which arrive on lead 108, this being performed by using the reference clock on lead 116, and to produce a signed difference signal between the measured value and the predetermined reference value, as well as a difference output timing signal. Both of these signals appear on lead 124.

Figure 4:
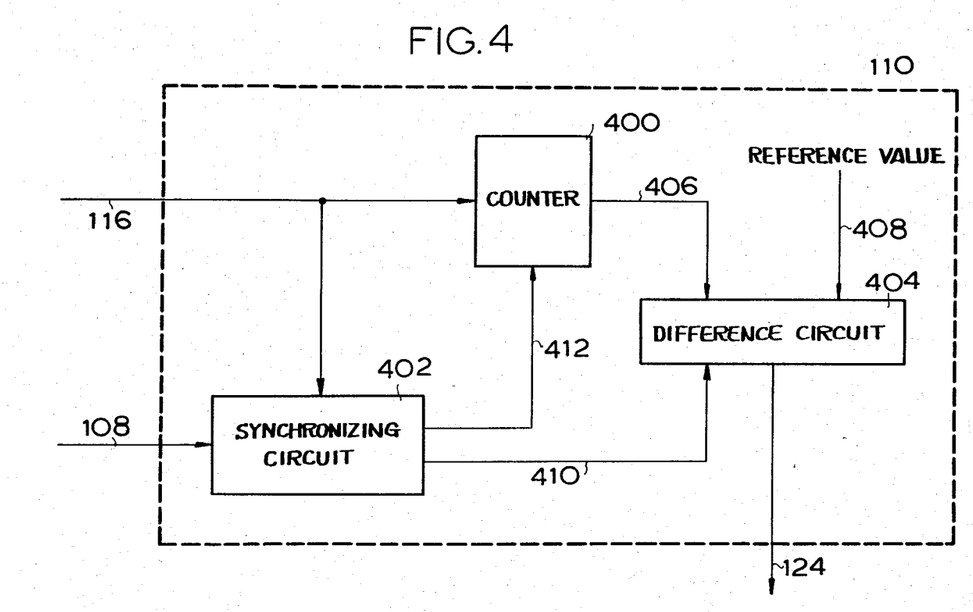
FIG. 4 is a block diagram showing the details of an arithmetic circuit for error evaluation.

The construction of arithmetic circuit 110 is shown in greater detail in FIG. 4. A counter, designated at numeral 400, measures the time interval of the drop signal pulses which arrive on lead 108, this being accomplished by counting the pulses in the reference clock input at lead 116. A synchronizing circuit 402 produces two successive signal pules obtained by synchronizing the leading edge of the drop signal to the reference clock. These signal pulses are delivered on leads 410, 412. That is, the earlier or preceding pulse is delivered on lead 410 to provide the timing at which a difference circuit, described below, is to compute a difference value. The latter or succeeding pulse is delivered on lead 412 to reset the count in counter 400. The difference circuit, designated at 404, ordinarily is realized through use of a binary adder. One input thereto is the count which counter 400 provides on lead 406. The other input is a predetermined fixed reference value, namely the value of the preset frequency, which is some multiple (30) of the drop rate. In other words, the reference value is the number of pulses (30) to be counted in the interval between the generation of drop signal pulses when the drop conditions are normal. The reference value can be entered on lead 408 in the form of a combination of binary (high and low level) values or through use of a dip switch or the like.

The output lead 124 of the arithmetic circuit 110 is connected to an arithmetic circuit 126 for computing the amount of regulation or control to be applied to adjust the flow rate, as will be described later. The arithmetic circuit 126 has two of its four output leads, namely leads 128 and 130, connected to the input side of a pinch clamp driving circuit 132. The latter circuit, which includes a stepping motor (not shown) or the like, is mechanically connected to a pinch clamp 134 for adjusting the flow rate of the infusion liquid through the flow passage constituted by the flexible tubing 100. The driving circuit 132 has three input leads 128, 130, 136 on which signals arrive that specify the amount of pinch clamp regulation, namely the rotating speed of the motor, the direction in which the pinch clamp 134 is to be regulated, namely the rotational direction of the motor, and the active state of the circuit 132, namely whether the motor is to start or stop. The arithmetic circuit 126, which receives the signed difference signal and the difference output timing signal from arithmetic circuit 110 over lead 124, responds to the signal on lead 124 by delivering the signal indicative of the amount of pinch clamp regulation via lead 128, the signal indicative of the direction of regulation via lead 130, the enable signal for starting the driving circuit 132 via lead 138, and the disable signal for stopping the driving circuit 132 via lead 140.

Figure 5:
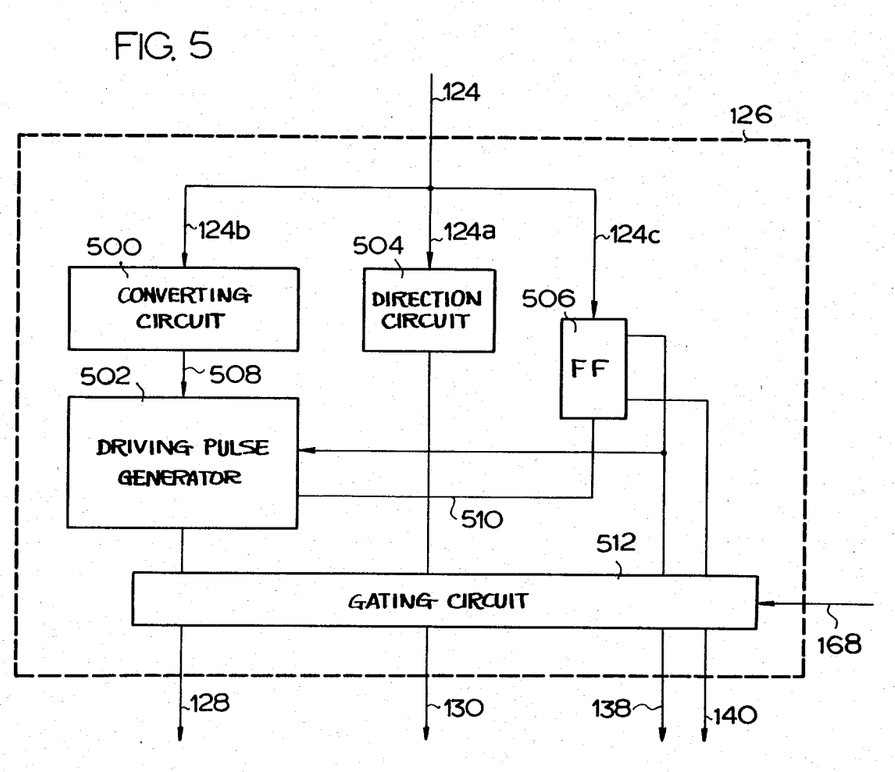
FIG. 5 is a block diagram showing the details of an arithmetic circuit for computing an amount of regulation.

Reference will now be had to FIG. 5 to describe the functioning of arithmetic circuit 126 in greater detail. The arithmetic circuit 126 includes a circuit 500 for converting the difference signal, received on input lead 124b, into a regulation factor, namely into a signal indicating the number of drive pulses that are to be applied to the pinch clamp drive, such as the stepping motor mentioned above. The signal indicative of the pulse number appears on lead 508. To make the conversion, the converting circuit 500 may employ a read-only memory (ROM) having various pulse numbers stored therein, and use the input difference signal to address the ROM in order to read out the corresponding pulse number as data. A flip-flop (FF) circuit 506 is set by the difference output timing signal that arrives on input lead 124c, and delivers an enable signal on output lead 138 via a gating circuit 512 to start the driving circuit 132. At the same time, FF 506 produces an enable signal which enables a driving pulse oscillator or generator 502 to begin delivering driving pulses. The driving pulse oscillator 502 receives on lead 508 the signal indicative of the number of driving pulses and delivers on output lead 128, via the gating circuit 512, a low-frequency pulsed signal indicative of a comparatively slow driving speed, the number of pulses delivered being equivalent to the number specified by the signal on lead 508. When the generation of the driving pulses ends, the oscillator 502 sends a reset signal to FF 506 on lead 510, whereby FF 506 is reset. When this occurs, a disable signal appears on output lead 140 via the gating circuit 512 to halt the operation of the driving circuit 132. A direction determining circuit 504 receives the signed signal on lead 124a and responds by producing a signal, which appears on output lead 130 via gating circuit 512, indicative of the direction in which the pinch clamp 134 is to be regulated. The gating circuit 512 is provided to allow the output of a signal generating circuit 164, described below, precedence over the output of arithmetic circuit 126 while the circuit 164 is in operation. The circuit 164 is adapted to generate a signal for forcibly closing the pinch clamp 134 at a relatively rapid rate. An alarm circuit 160 (FIG. 1), which is activated when an abnormality in the drop condition is sensed, produces a signal at such time to start the signal generating circuit 164, so as to close the pinch clamp 134. This will be described in further detail below. Since the control signal from the signal generating circuit 164 has a higher order of priority than the ordinary control signal from the arithmetic circuit 126, it is necessary that the gating circuit 512 (FIG. 5) be closed during the active period of the control signal from the generating circuit 164 to prohibit the delivery of the ordinary control signal from the arithmetic circuit 126. To achieve this, the signal which enters the gating circuit 512 on lead 168 becomes high (logic "1") during operation of the signal generating circuit 164, whereby the gating circuit 512 is closed to temporarily block all of the output signals from the arithmetic circuit 126. To realize this effect, a widely available tristate element may be used to construct the gating circuit 512.

Returning to FIG. 1, a fully-closed state position sensor 142, such as a microswitch, which responds to produce a signal when the flexible tube 100 is fully closed, is provided at the location of the pinch clamp 134 to sense the fully-closed position of the clamp. The output of the sensor 142 on lead 144 is connected to the first input terminal of an OR gate 146. Connected to the second input terminal of the OR gate 146 is lead 140 from the arithmetic circuit 126. Connected to the third input terminal of OR gate 146 is a lead 148 for introducing a stop signal SP to halt the operation of the driving circuit 132. The signal is produced by a manual operation, as by closing a manual switch, not shown. The output lead 150 of OR gate 146 is connected to one input terminal of a start/stop circuit 152. The other input to the start/stop circuit 152 is the output of an OR gate 156 that arrives on lead 154.

A drop interval measuring circuit 112 includes a resettable counter, by way of example, and functions as a timer which is reset by the drop signal pulses 202 that arrive on lead 108. The circuit 112 is adapted to produce a signal on lead 158 when the most recent drop signal pulse 202 on lead 108 is not followed by another drop signal pulse 202 within a predetermined period of time which, by way of example, may be equivalent to 40 times the period of the reference lock 200 corresponding to the drop rate set by the setting device 120. The output of the drop interval measuring circuit 112 on lead 158 is connected to the alarm circuit 160 which, upon receiving the signal from circuit 112, produces a signal on lead 162. The alarm circuit 160 may be equipped with a buzzer or lamp (not shown) to produce an audible or visual indication in response to the signal on lead 158.

Lead 162 from alarm circuit 160 is connected to one input terminal of a drop counter 114 and to the input side of the signal generating circuit 164, so that both of these circuits may be activated by the signal from the alarm circuit. The drop counter 114 also comprises a resettable counter which, once started by the signal on lead 162, begins counting the drop signal pulses 202 that arrive at its other input terminal via lead 108. When the count reaches a predetermined value of, say, six, the counter 114 produces a high-level signal on lead 166. This lead is connected to the input of OR gate 156, alarm circuit 160 and signal generating circuit 164.

The signal generating circuit 164 responds to the signal from the alarm circuit 160 on lead 162 by generating a signal for closing the pinch clamp 134 with relative abruptness. More specifically, when a signal arrives from the alarm circuit, the signal generating circuit 164 produces a signal on lead 168, connected to the input side of OR gate 156, to start the driving circuit 132, produces high-frequency driving signal pulses on lead 128 to rotate the motor (not shown) of the driving circuit 132 at a comparatively high speed, and produces a signal on lead 130 instructive of the fact that the pinch clamp 134 is to be driven in the closing direction. The signal generating circuit 164 is reset along with the alarm circuit 160 by the output signal of the drop counter 114 that appears on lead 166.

The fourth input terminal of OR gate 156 is connected to a lead 170 for receiving a start signal ST to activate the driving circuit 132. The signal ST is produced by manual operation, such as by closing a manual switch, not shown.

The operation of the infusion control apparatus illustrated in FIG. 1 will now be described in conjunction with the waveform diagram of FIG. 2 and the flow chart shown in FIG. 3.

First, with the pinch clamp 134 in the fully closed state, the start signal ST is introduced on lead 170 by operating a switch or the like, whereupon the pinch clamp driving circuit 132 is actuated by the start/stop circuit 152 to gradually begin opening the pinch clamp. This corresponds to time a in FIG. 2, and to step 300 in FIG. 3. As a result, the drops of infusion liquid 122 begin falling within the drop chamber 102 and fall at a gradually faster rate, giving rise to drop signal pulses 202 on lead 108 that occur at increasingly shorter intervals. The arithmetic circuit 110 measures the time interval between the pulses 202 on the basis of the reference clock applied on lead 116, performs an arithmetic operation to find the difference between the measured value and the reference value (step 302 in FIG. 3), and produces a signal on lead 124 that corresponds to the error in the measured pulse interval. The arithmetic circuit 126 generates signals on leads 128, 130, 138, 140 in accordance with the error signal on lead 124 (step 304 in FIG. 3). At time b in FIG. 2, the number of reference clock pulses counted in arithmetic circuit 110 coincides with the reference value. Up to that point, however, the reference value is the smaller of the two, so that the arithmetic circuit 126 produces, on lead 128, a driving pulse signal of such a frequency as will drive the pinch clamp 134 at a comparatively slow driving speed, a signal, on lead 130, instructive of the fact that the clamp is to be driven in the opening direction, and a start signal on lead 138 (block 306, FIG. 3).

When the actually measured drop rate in drop chamber 102 coincides with the drop rate set by setting unit 120 (time b in FIG. 2), the error signal produced by arithmetic circuit 110 becomes zero, and arithmetic circuit 126 produces and holds a disable signal on lead 140 (time b, step 308). This condition is sustained as long as the infusion liquid is falling at the set drop rate (time b to time c).

Assume now that the flow passage constituted by the flexible tubing 100 leading to the patient (not shown) starts being closed off due to a change in the external conditions, as may be caused by the patient bending his arm or by a small air bubble forming within the tubing. When this occurs there is an increase in the time interval between the drops 122, whereby the interval between the drop signal pulses 202 lengthens (time c to time d). The arithmetic circuit 110 senses this condition, which is reflected in the error signal on lead 124. The arithmetic circuit 126 consequently delivers the aforementioned signals via leads 128, 130, 138, actuating the driving circuit 132 so as to gradually open the pinch clamp 132 to a wider degree. Now assume that the cause of the tube constriction is removed at a certain time, say at d in FIG. 2. When this occurs the result can be a continuous flow of the liquid in drop chamber 102. In such an event, the level of the drop signal becomes flat or continuous, as indicated at 204 in FIG. 2, so that the pulses 202 are no longer detected by the measuring circuit 112 within the predetermined period of time (block 310, FIG. 3). This results in circuit 112 delivering a signal via lead 158, thereby actuating the alarm circuit 160 (time e).

Figure 3:
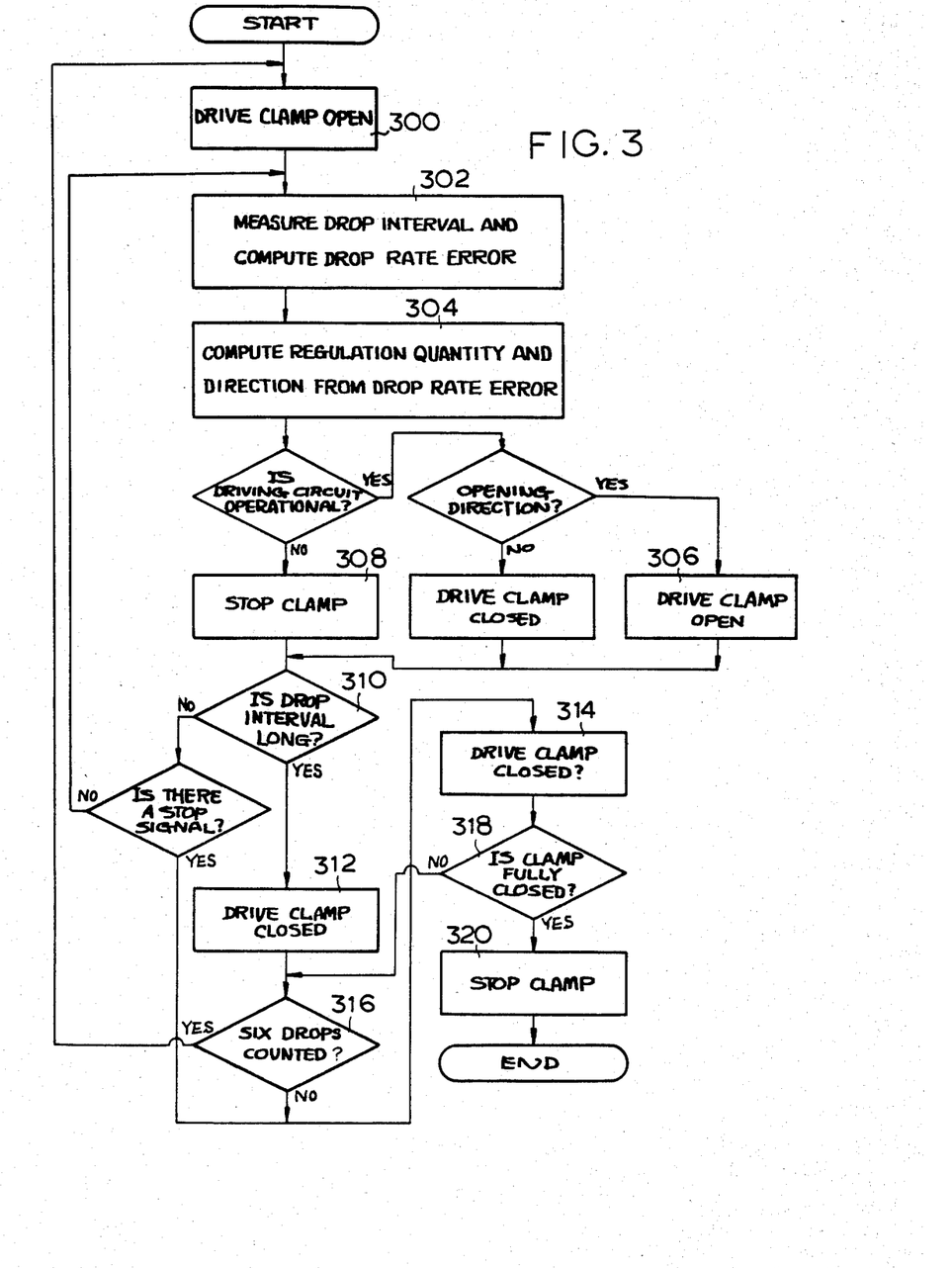
FIG. 3 is a flow chart illustrating the operation of the apparatus shown in FIG. 1.

The alarm circuit 160 produces a signal on lead 162, actuating the drop counter 114 so that the counter may start counting any drop signal pulses 202 that will arrive via lead 108, and actuating the signal generating circuit 164 which responds by initiating operations for closing the pinch clamp 134 (steps 312, 314 in FIG. 3). That is, the signal generating circuit 164 delivers, via lead 128, a driving pulse signal of such a frequency as will rotate the motor of driving circuit 132 at a comparatively high speed, a signal, via lead 130, indicating that the pinch clamp 134 is to be driven in the closing direction, and a signal, via lead 168, for starting the driving circuit 132 and for blocking the output signals from the arithmetic circuit 126. The result of the foregoing operations is that the pinch clamp 134 starts closing at a comparatively rapid rate (time f to time g). As the flow passage through tubing 100 is constricted by the pinch clamp 134, the hitherto continuous nature of the flow in drop chamber 122 reverts to a drop-wise flow (time f). Since the pulses 202 consequently reappear in the drop signal on lead 108, there are now pulses for the counter circuit 114 to count. When the counter 114 counts up a prescribed number (six) of these pulses (step 316 in FIG. 3), a signal appears on lead 166 to reset the alarm circuit 160 and the signal generating circuit 164, and to actuate the start/stop circuit 152 via the OR gate 156, whereby the clamp driving circuit 132 becomes operational (time g, block 300). It should be noted that the pinch clamp 134 may reach the fully closed position, or that the infusion liquid reservoir (not shown) upstream of the drop chamber 102 may run out of liquid, before the counter 114 has a chance to count the prescribed number of pulses 202, namely six in this instance. In the former case, the sensor 142 such as a microswitch will act before the counter 114 produces the signal on lead 166, thereby delivering a signal (block 318, FIG. 3) via lead 144 that disables the driving circuit 132 to stop the pinch clamp 134 at the fully closed position. In the latter case, namely where the liquid in the reservoir is depleted, the condition naturally is a sustained one, so that the system will not restart from the initial state. The same will be true in any other case where, for some reason, the counter 114 cannot be counted up to the prescribed value by the drop signal pulses 122. Furthermore, in a case where the drop counter 114 counts the prescribed number of drop signal pulses 122 before the pinch clamp 134 reaches the fully closed position (as at time g in FIG. 2), the driving circuit 132 is enabled via lead 166, OR gate 156 and start/stop circuit 152, thereby restarting the system from the prevailing condition and effecting the transition to normal operation to allow regulation of the pinch clamp opening (step 300, FIG. 3).

As to the effects of the infusion control apparatus according to the present invention, the foregoing construction assures that the occurrence of a continuous flow in the drop chamber, regardless of the cause, will be detected and remedied by restoring the flow to a drop-wise condition, namely to the initially set drop rate, in a very short period of time. This makes possible an extremely safe drop-wise infusion operation without human intervention, while at the same time minimizing the psychological effects of frequent alarms on the patient. Since the detection of abnormalities and the restoration of the normal drop-wise condition are realized through ordinary logic elements and circuitry, and since detection of the drop-wise state is performed by a photoelectric converting element, the apparatus operates stably and is low in cost, and can be applied without limitations being imposed by the geometery of the drop chamber. The flow passage can also be sealed off with assurance when the liquid reservoir is depleted of liquid.

As many apparently widely different embodiments of the present invention can be made without departing from the spirit and scope thereof, it is to be understood that the invention is not limited to the specific embodiments thereof except as defined in the appended claims.

What I claim is:

1. An apparatus for controlling drop-wise infusion of an infusion liquid through a flow passage, wherein a drop chamber is provided upstream of the flow passage, the apparatus comprising:

input means arranged to be operatively associated with the drop chamber for forming an input signal on the basis of a change in a quantity of light received by said input means after the light is passed through falling drops of the infusion liquid in the drop chamber, wherein an absence of said input signal indicates either one of an exhaustion in supply of the infusion liquid or a continuous stream of liquid falling in the drop chamber;

flow adjusting means arranged to interact with the flow passage for adjusting the flow of infusion liquid in the flow passage;

drop interval control means coupled to said input means adapted to evaluate the interval between successive falling drops of infusion liquid in the drop chamber in response to said input signal, for producing a control signal operative to establish a drop interval adjustment mode wherein said flow adjusting means adjusts the flow of infusion liquid to bring said interval into correspondence with a set value;

cut-off means coupled to said drop interval control means and to said flow adjusting means for establishing a liquid cut-off mode wherein the flow of infusion liquid through the flow passage is closed off by said flow adjusting means upon detecting the absence of said input signal over a predetermined period of time, said cut-off means providing a corresponding output to said flow adjusting means; and drop count means coupled to said input means and to said cut-off means for detecting said input signal after initiation of said cut-off mode, wherein said drop count means produces a signal to restore said flow adjusting means to operate in said drop interval adjustment mode when said input signal indicates a set number of drops have fallen in the drop chamber after the flow of infusion liquid through the flow passage is closed off by said flow adjusting means in said cut-off mode, so that said flow adjusting means remains in said cut-off mode if the supply of infusion liquid is exhausted, and is restored to said drop interval adjustment mode if said set number of drops fall in the drop chamber after the flow passage is closed off in the absence of said input signal over said predetermined period of time.

2. An apparatus according to claim 1, further comprising priority deciding means coupled to said cut-off means for giving the output from said cut-off means a higher order of priority to operate said flow adjusting means than said control signal from said drop interval control means.

3. An apparatus according to claim 1, including a transparent drop chamber, and said input means comprises a light source and a light-receiving element disposed to confront each other across said transparent drop chamber in which the infusion liquid drops, said light-receiving element receiving light from said light source.

4. An apparatus according to claim 1, in which said cut-off means includes alarm means arranged to be actuated upon detecting the absence of said input signal over a predetermined period of time.

5. An apparatus according to claim 1, in which said flow adjusting means comprises sensing means for sensing full closure of the flow passage, and inhibit means coupled to said sensing means for inhibiting the control signal from said drop interval control means and the output from said cut-off means in response to detection of full closure by said sensing means.

6. An apparatus according to claim 2, wherein said priority deciding means includes a tristate element.

7. An apparatus according to claim 5, wherein said sensing means comprises a microswitch.

* * * * *